United States Patent
Chawla

(10) Patent No.: US 11,631,494 B2
(45) Date of Patent: Apr. 18, 2023

(54) SYSTEM AND METHOD FOR MONITORING INSTALLED HEALTHCARE ASSETS

(71) Applicant: GE Precision Healthcare LLC, Wauwatosa, WI (US)

(72) Inventor: Himanshu Chawla, Bangaluru (IN)

(73) Assignee: GE Precision Healthcare LLC, Wauwatosa, WI (US)

( * ) Notice: Subject to any disclaimer, the term of this patent is extended or adjusted under 35 U.S.C. 154(b) by 696 days.

(21) Appl. No.: 16/701,891

(22) Filed: Dec. 3, 2019

(65) Prior Publication Data

US 2021/0166809 A1 Jun. 3, 2021

(51) Int. Cl.
| | | |
|---|---|---|
| *G16H 40/40* | (2018.01) | |
| *G06F 16/906* | (2019.01) | |
| *G06F 17/12* | (2006.01) | |
| *G05B 23/02* | (2006.01) | |

(52) U.S. Cl.
CPC ........... *G16H 40/40* (2018.01); *G05B 23/024* (2013.01); *G06F 16/906* (2019.01); *G06F 17/12* (2013.01)

(58) Field of Classification Search
CPC ........ G16H 40/40; G16H 40/00; G16H 40/67; G05B 23/024; G05B 23/0224; G05B 23/0205; G05B 23/02; G05B 23/00; G05B 23/0283; G05B 23/0259; G06F 16/906; G06F 16/90; G06F 16/00; G06F 17/12; G06F 17/11; G06F 17/10; G06F 17/00
See application file for complete search history.

(56) References Cited

U.S. PATENT DOCUMENTS

| | | | |
|---|---|---|---|
| 9,734,001 B2 | 8/2017 | Das et al. | |
| 2004/0176887 A1 | 9/2004 | Kent et al. | |
| 2009/0254362 A1* | 10/2009 | Choubey | G16H 40/20 705/2 |
| 2020/0118053 A1* | 4/2020 | Chapin | G06Q 10/06315 |
| 2020/0160207 A1* | 5/2020 | Song | G06F 11/3466 |

OTHER PUBLICATIONS

IBM Services, Predictive maintenance breakdown. Stay up and running. Control costs., Jan. 21, 2019, Accessed from https://www.ibm.com/services/technology-support/multivendor-it/predictive-maintenance.

* cited by examiner

*Primary Examiner* — Mohamed Charioui
(74) *Attorney, Agent, or Firm* — Andrus Intellectual Property Law, LLP

(57) ABSTRACT

A system for monitoring installed healthcare assets includes an asset database containing installed asset data and recovered asset data and a storage system storing a trained regression model and a clustering model. A processing system is configured to process the installed asset data using the trained regression model to predict a recovery time for each installed healthcare asset and process the installed asset data and the recovered asset data using the clustering model to identify a set of target assets, wherein the set of target assets is subset of the installed healthcare assets. The processing system is further configured to identify at least one recovery target asset based on the set of target assets and the predicted recovery time for each installed healthcare asset in the set of target assets.

20 Claims, 7 Drawing Sheets

| System ID | Install date | Deinstall date | Features....columns | Lifespan |
|---|---|---|---|---|
| 2763658 | t | t + n | All features up to t + n | 100% |

Segment 1:

| System ID | Install date | Deinstall date | Features....columns | Lifespan |
|---|---|---|---|---|
| 2763658 | t | t + n | All features up to t + 1 * n/10 | 10% |

Segment 2:

| System ID | Install date | Deinstall date | Features....columns | Lifespan |
|---|---|---|---|---|
| 2763658 | t | t + n | All features up to t + 2 * n/10 | 20% |

Segment 3:

| System ID | Install date | Deinstall date | Features....columns | Lifespan |
|---|---|---|---|---|
| 2763658 | t | t + n | All features up to t + 3 * n/10 | 30% |

. . . .

Segment 10:

| System ID | Install date | Deinstall date | Features....columns | Lifespan |
|---|---|---|---|---|
| 2763658 | t | t + n | All features up to t + n | 100% |

FIG. 5

| System ID | Region | Quarter | Cluster | Age | Install date | In co |
|---|---|---|---|---|---|---|
| ### | USCAN | Others | 2 | 1.556164384 | 18-12-2017 00:... | |
| ### | USCAN | 2020 Q3 | 2 | 1.402739726 | 12-02-2018 00:... | |
| ### | USCAN | Others | 2 | 1.62739726 | 22-11-2017 00:... | |
| ### | USCAN | 2020 Q3 | 2 | 1.282191781 | 28-03-2018 00:... | |
| ### | USCAN | 2020 Q2 | 2 | 1.147945205 | 16-05-2018 00:... | |
| ### | USCAN | 2020 Q3 | 2 | 1.221917808 | 19-04-2018 00:... | |
| ### | USCAN | Others | 1 | 1.854794521 | 31-08-2017 00:... | |
| ### | USCAN | 2020 Q3 | 2 | 1.169863014 | 08-05-2018 00:... | |
| ### | USCAN | Others | 2 | 1.761643836 | 04-10-2017 00:... | |
| ### | USCAN | Others | 2 | 1.421917808 | 05-02-2018 00:... | |
| ### | USCAN | Others | 2 | 1.613698630 | 27-11-2017 00:... | |
| ### | USCAN | Others | 2 | 1.520547945 | 31-12-2017 00:... | |
| ### | USCAN | 2020 Q1 | 2 | 0.528767123 | 28-12-2018 00:... | |

FIG. 8

SYSTEM AND METHOD FOR MONITORING INSTALLED HEALTHCARE ASSETS

BACKGROUND

The present disclosure generally relates to systems and methods for monitoring installed healthcare assets, and more particularly to systems and methods for prognostic analysis of healthcare assets for identifying appropriate assets to be recovered and/or identifying an appropriate time to recover assets.

Healthcare assets, such as Computer Tomography (CT) imagers, Magnetic Resonance (MR) imagers, Position Emission Tomography (PET) imagers, etc. are widely used for diagnosis, treatment, and monitoring of patients. Healthcare facilities, such as hospitals and clinics, are heavily dependent on the operation, efficiency, and performance of these assets. Failure of these healthcare assets cannot be afforded, and thus many healthcare assets are subjected to preventative maintenance which involves periodic maintenance and repair or replacement of key elements of such assets. Often, as an asset approaches or exceeds its expected period of operation, or expected lifespan, healthcare assets are recovered by asset suppliers. The recovered healthcare assets may be refurbished and resold or salvaged for purposes of repairing other similar healthcare assets.

SUMMARY

This Summary is provided to introduce a selection of concepts that are further described below in the Detailed Description. This Summary is not intended to identify key or essential features of the claimed subject matter, nor is it intended to be used as an aid in limiting the scope of the claimed subject matter.

One embodiment of a system for monitoring installed healthcare assets includes an asset database containing installed asset data and recovered asset data, wherein the installed asset data comprises feature values describing installed healthcare assets and recovered asset data comprises feature values describing uninstalled healthcare assets that were recovered, as well as a storage system storing a trained regression model and a clustering model. A processing system is configured to process the installed asset data using the trained regression model to predict a recovery time for each installed healthcare asset and process the installed asset data and the recovered asset data using the clustering model to identify a set of target assets, wherein the set of target assets is subset of the installed healthcare assets. The processing system is further configured to identify at least one recovery target asset based on the set of target assets and the predicted recovery time for each installed healthcare asset in the set of target assets.

One embodiment of a computer-implemented method of monitoring installed healthcare assets includes storing healthcare asset data that includes installed asset data comprising feature values describing installed healthcare assets and recovered asset data comprising feature values describing uninstalled healthcare assets that were recovered and then processing that data with trained models to determine at least on recovery target asset. Using a trained regression model, a recovery time is predicted for each installed healthcare asset based on the installed asset data. Using a clustering model, a set of target assets is identified based on the installed asset data and the recovered healthcare data, wherein the set of target assets is subset of the installed healthcare assets. At least one recovery target asset is then identified based on the set of target assets and the predicted recovery time for each installed healthcare asset in the set of target assets.

In another embodiment, a method of predicting a recovery time for an installed healthcare asset includes storing installed healthcare asset data, wherein the installed asset data comprises feature values describing installed healthcare assets, and storing recovered asset data, wherein recovered asset data comprises feature values describing uninstalled healthcare assets that were recovered. A linear regression model is then trained using the recovered asset data, wherein the trained regression model is configured to predict a lifespan of a healthcare asset based on at least one of the feature values describing the healthcare asset. The trained regression model is then utilized to generate a predicted recovery time for each installed healthcare asset based on the installed asset data.

Various other features, objects, and advantages of the invention will be made apparent from the following description taken together with the drawings.

BRIEF DESCRIPTION OF THE DRAWINGS

The present disclosure is described with reference to the following Figures.

FIG. 5 illustrates exemplary asset database storing healthcare asset data according to one embodiment of the present disclosure;

FIG. 8 illustrates exemplary output of an asset recovery module listing recovery target assets to be recovered.

DETAILED DESCRIPTION

Figure 1:
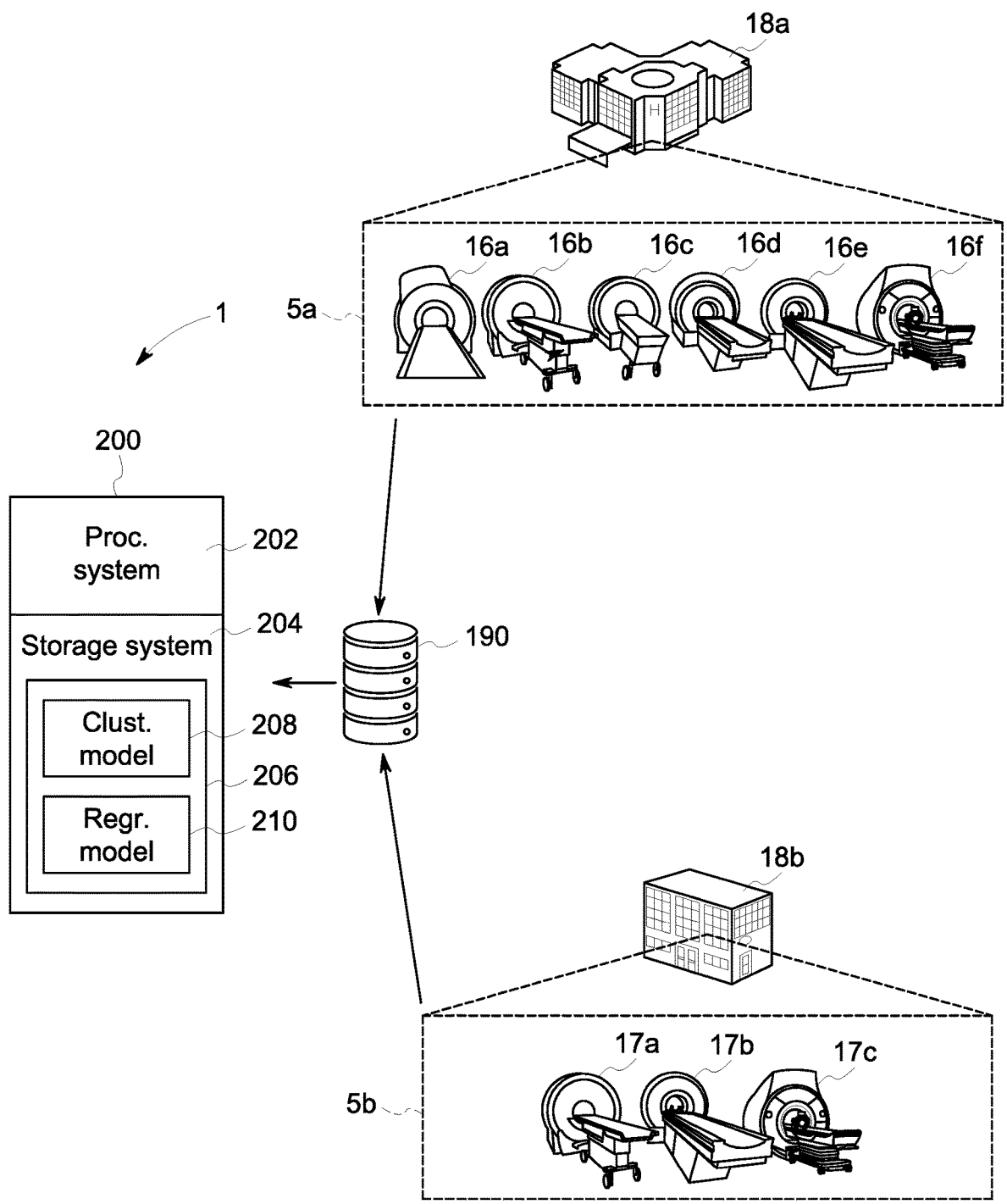
FIG. 1 exemplifies a system for monitoring installed healthcare assets according to one embodiment of the present disclosure.

The inventors have recognized a need for a system and method for identifying installed healthcare assets in need of recovery. Healthcare assets, such as CT imagers, MR imagers, PET imagers, etc. are critical to provision of healthcare, and thus the proper functioning of these healthcare assets is of high importance to healthcare providers. Healthcare asset manufacturers and sellers need a way of identifying healthcare assets in the field which are prime targets for recovery and replacement. This helps those manufacturers maintain and/or grow their install base, and it helps healthcare providers avoid failure of their installed assets. The inventors have recognized that identifying target healthcare assets that are prime candidates for recovery is complicated by many factors, such as diverse usage amounts and maintenance schedules across asset owners. Too often, asset uninstallation and recovery comes after asset failure, which can ruin relationships between customers (e.g. healthcare facilities and providers) and asset manufacturers/sellers. This leads to a significant cost to healthcare facilities, decreased patient care, and lost revenue to manufacturers/sellers.

In view of the problems and challenges recognized in the relevant art by the inventors, they have developed a system and method that performs prognostic analysis of healthcare assets for recovery. The disclosed system utilizes a combination of supervised and unsupervised learning to identify target assets that should be recovered and to predict the timeframe in which those assets should be recovered. A recovered asset is one that is reclaimed by an asset vendor (e.g., General Electric, Siemens, Philips, etc.), where the asset is uninstalled and then refurnished or harvested for replacement parts (e.g., see FIG. 4 and corresponding description). The disclosed system and method utilize asset data that includes feature values describing, for example, asset age, service, history and patterns, facility information relating to the healthcare facility in which the healthcare asset is installed, operation history information about the use and performance of the particular healthcare asset, and customer demographic data such as location and financial status of the customer, etc.

The asset data is processed by both an unsupervised clustering model and a supervised regression model. The clustering model is trained to identify critical assets for recovery. For example, the clustering model may be a partitioning around medoids (PAM) clustering model. The regression model is trained to learn the failure patterns of uninstalled and recovered assets by defining the features for different timeframes of the assets' lifetime and training on those timeframes. For example, the regression model may be a trained linear regression model configured to predict a lifespan of the healthcare asset based on the feature values of the recovered asset data describing the uninstalled and recovered assets. This model can then be used to predict a recovery time for installed assets on the field. The recovery time generated by the trained regression model and the target assets identified by the clustering model can then be combined to identify recovery target assets, which are installed healthcare assets that are in need of recovery and exhibit features that indicate that they are likely recoverable. This system and method will reduce unplanned downtime of healthcare assets at healthcare facilities and will assist asset manufacturers/sellers in recovering assets, which they can refurbish or salvage, and may provide opportunity for the sale of new assets to replace the recovered assets.

FIG. 1 depicts an exemplary embodiment of a system 1 for monitoring installed healthcare assets. In the example, two different healthcare facilities 18*a* and 18*b* each have a set of monitored assets 5*a* and 5*b*. In various embodiments, each set of healthcare assets 5*a* and 5*b* may include different types of assets and numbers of assets, which may be provided by a single manufacturer or by two or more different manufacturers. For example, each set of monitored assets 5*a*, 5*b* may include one or more of a CT imager, an MR imagers, a PET imager, and/or other types of imaging devices, patient monitoring devices, etc. Thus, each monitored asset 16 (e.g., 16*a*-16*f*, 17*a*-17*c*) in each healthcare facility 18 (e.g., the first healthcare facility 18*a* and the second healthcare facility 18*b*) may be any type of patient imager, patient monitoring device, or other type of installed healthcare asset installed at the respective healthcare facility 18 (e.g., hospitals, outpatient care facilities, imaging centers, specialized care centers, etc.).

Data is collected about each healthcare asset 16*a*-16*f* and 17*a*-17*c* through the full lifespan of that asset, and all such data is stored in an asset database 190. The installed asset data is then processed to identify at least one recovery target asset, wherein each recovery target asset is an asset (e.g. one of 16*a*-16*f* or 17*a*-17*c*) which should be recovered based on its age and/or maintenance history, for example, and also matches data features of assets that have been previously recovered. Thus, the system 1 includes software for processing installed asset data to identify at least one recovery target asset. Each system comprises an asset recovery module 206 which is a set of computer-executable instructions stored in a storage system 204 of a computing system 200 and configured to process installed asset data to identify one or more recovery target assets. The asset recovery module 206 may be configured to retrieve and process installed asset data stored in the asset database 190. In various embodiments, the asset database 190 may be stored in the storage system 204, or may be stored in a separate storage system.

The computing system 200 that includes a processing system 202, storage system 204, and software. The processing system 202 loads and executes software from the storage system 204, including the asset recovery module, which are software applications or other sets of computer executable instructions. Each of the modules 12, 14, 16 include computer-readable instructions that, when executed by the processing system 202, direct the processing system 202 to operate as described in herein The processing system 202 includes one or more processors, which may be a microprocessor, a general purpose central processing unit, an application-specific processor, a microcontroller, or any type of logic-based device. The processing system 202 may also include circuitry that retrieves and executes software from storage system 204. Processing system 202 can be implemented within a single processing device but can also be distributed across multiple processing devices or sub-systems that cooperate in executing program instructions. The storage system 204 can comprise any storage media, or group of storage media, readable by processing system 202 and capable of storing software. The storage system 204 can include volatile and non-volatile, removable and non-removable media implemented in any method or technology for storage of information, such as computer-readable instructions, data structures, program modules, or other data. Storage system 204 can be implemented as a single storage device but may also be implemented across multiple storage devices or sub-systems. In certain embodiments, the asset database 190 may be incorporated and stored within the storage system 204, or may be stored on a separate storage system.

The asset recovery module 206 may include an unsupervised learning module and a supervised learning module utilized in parallel to process the installed asset data. In one embodiment, an unsupervised clustering model 208 is trained to identify a set of target assets that have similar asset data patterns or features to recovered asset data regarding healthcare asset that have already been recovered. A trained regression model 210 is trained to predict recovery time for each installed healthcare asset. The results of the trained regression model 210 and the clustering model 208 are then combined to identify the recovery target assets.

Figure 3:
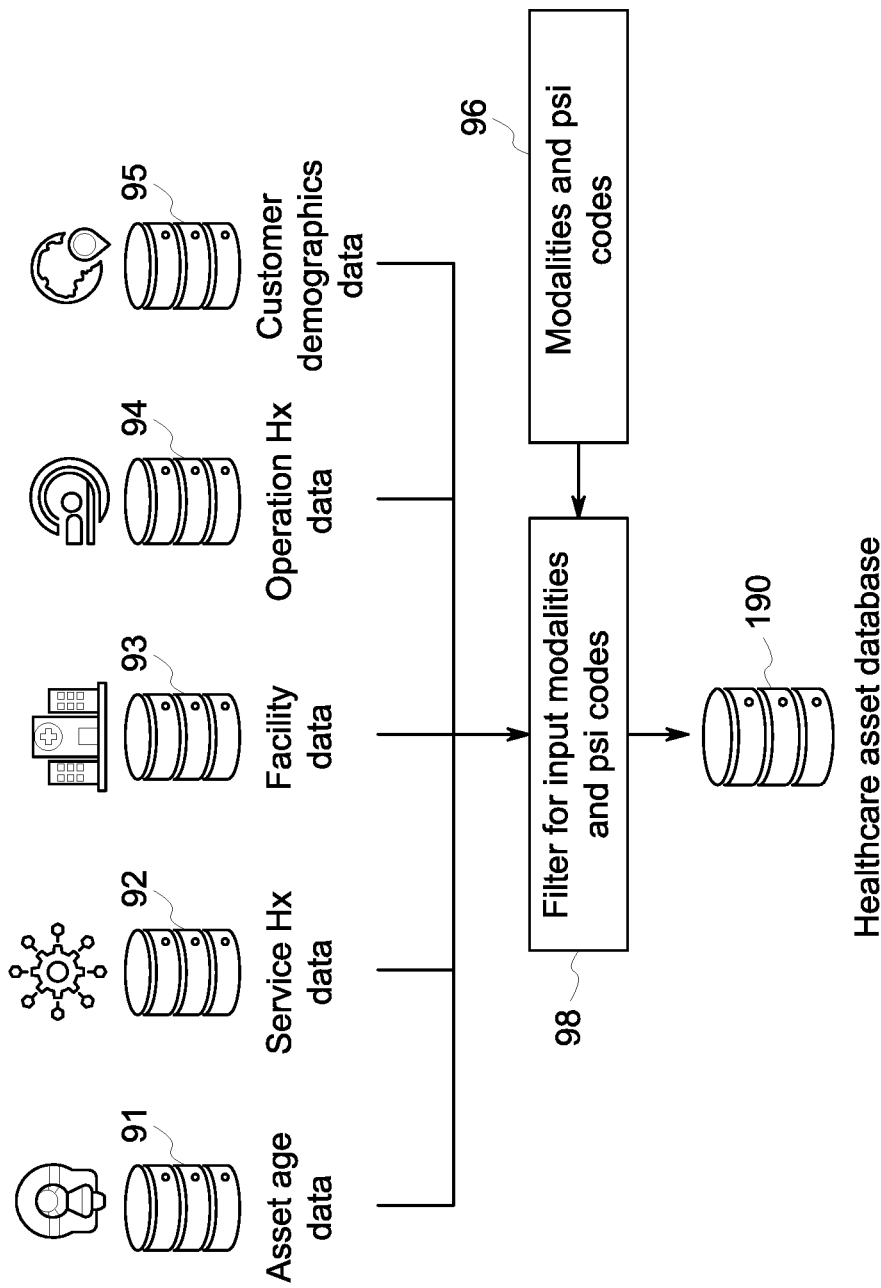
FIG. 3 is a schematic diagram illustrating one embodiment of the healthcare asset database.

The asset database 190 includes asset data regarding installed assets, such as 16*a*-16*f* and 17*a*-17*c*, as well as recovered asset data describing assets that have been uninstalled and recovered. The asset data includes feature values describing the age, services, and other aspects of each healthcare asset. FIG. 3 illustrates an exemplary embodiment of asset data in the database 190. For each healthcare asset 16, 17, the asset data may include identified feature values describing asset age, service history, the facility at which the asset is installed, operation history data describing the operation history of the respective asset, and customer demographics data about the asset owner.

For example, the asset database 190 may include asset age data 91 for each healthcare asset, where asset age data includes values describing or indicating the age of the respective asset (when it was manufactured, when it was installed, the age of key parts of the healthcare asset, whether the asset is under warranty and for how long, whether the asset is under a service contract and for how long, and the like. The asset database 190 may further include service history data 92 describing the service history of the respective asset, including what components have been serviced or replaced and when, how many times said components have been replaced, the frequency and/or dates of routine service checks, etc. The asset database 190 may further include facility data 93, such as how many beds are in the healthcare facility (e.g. 18*a*, 18*b*) where the healthcare asset is installed, an average number of patients treated at that facility, the hospital configuration (such as what types of wards or services are provided at the healthcare facility), how many total assets that healthcare facility has, etc. The asset database 190 may further include operation history data 94 for each respective asset, such as how many image scans for patient treatments have been performed by the respective asset, how many operation hours the asset has performed, the types of operations performed in those operation hours, etc. Finally, the healthcare asset database 190 may further include customer demographic data for the customers of each asset, such as the insulation location (e.g. city and/or address), previous purchases by that asset owner, the number of assets owned by that customer and/or the duration of ownership or relationship with the customer, the purchasing history of that customer, etc.

Additionally, the modalities and PSI codes 96 are imputed. The modalities define the features to be extracted from the various data and PSI (planning sales inventory) codes are unique ID's to identify group of asset ID's under a product line. The data is then filtered at filter 98 for input modalities and PSI codes in order to extract certain features for each asset from the respective asset data. Feature extraction may include extracting one or more features, such as age, number of services, service contract flags, warranty flags, region, part information, etc. Asset age may be calculated using rules based on manufacture date plus data entry patterns by field engineers indicating age of key parts, etc.

Service history data describes when and how an asset has been serviced. Number of services for an asset may be calculated by filtering major services, like component replacements and repairs that directly affect the age and quality of the product and the frequency of those services. Service contract flags may be detected that tell the status of the service contract for an asset. If a machine is under a service contract it hints that the customer might not agree for uninstallation and recovery of that asset. Thus, this may mitigate against flagging the asset as a recovery target. Warranty flags may also be identified illustrating the warranty status of the asset. Here again, assets under warranty may be less likely to be recoverable. Part information for each asset includes identification of parts that are replaced during services. In one embodiment, the feature values extracted from part information may include a list of top parts for each asset the age or service status of that part. This feature is important because replacement of a key part, or a part that is a typical failure point for an asset, directly effects the lifespan of that asset Facility data includes information about a facility, such as feature values describing size and functionality of a healthcare facility 18 where the asset is installed. For example, the hospital bed count may be determined using a hospital identification look up table.

Operation history data includes feature values that describe how and how much an asset has been used, such as real time statistics (RTS) data. For example, the operation history data for an MR or CT imager may include a gantry data, number of spits for an x-ray tube, cam motor position for collimator, number of scans conducted, scan time or average time duration per scan, or other information that provides information about asset usage. This provides information about the actual usage of the asset, rather than just age which indicates generic wear and tear of a machine.

Customer demographics data may include information regarding location of a facility and or information relevant to historical relationships with asset venders. This dataset may add feature values not easily determined from standard hospital/facility identification info. Region, such as geographical location or region, adds an important perspective to the model because it highlights different demand and usage patterns of those assets. Assets in larger, more densely populated cities may be used more frequently, for example. Similarly, hospital bed count is a good approximation of the size and economic status of a hospital and may be indicative of the willingness of the customer, or asset owner, to allow recovery of the asset and invest a new asset. Number of assets owned by the customer or facility and number of previous such assets owned from the same asset vendor. Other features may be extracted from the asset database, as will be understood by a person having ordinary skill in the art in view of this disclosure.

Figure 4:
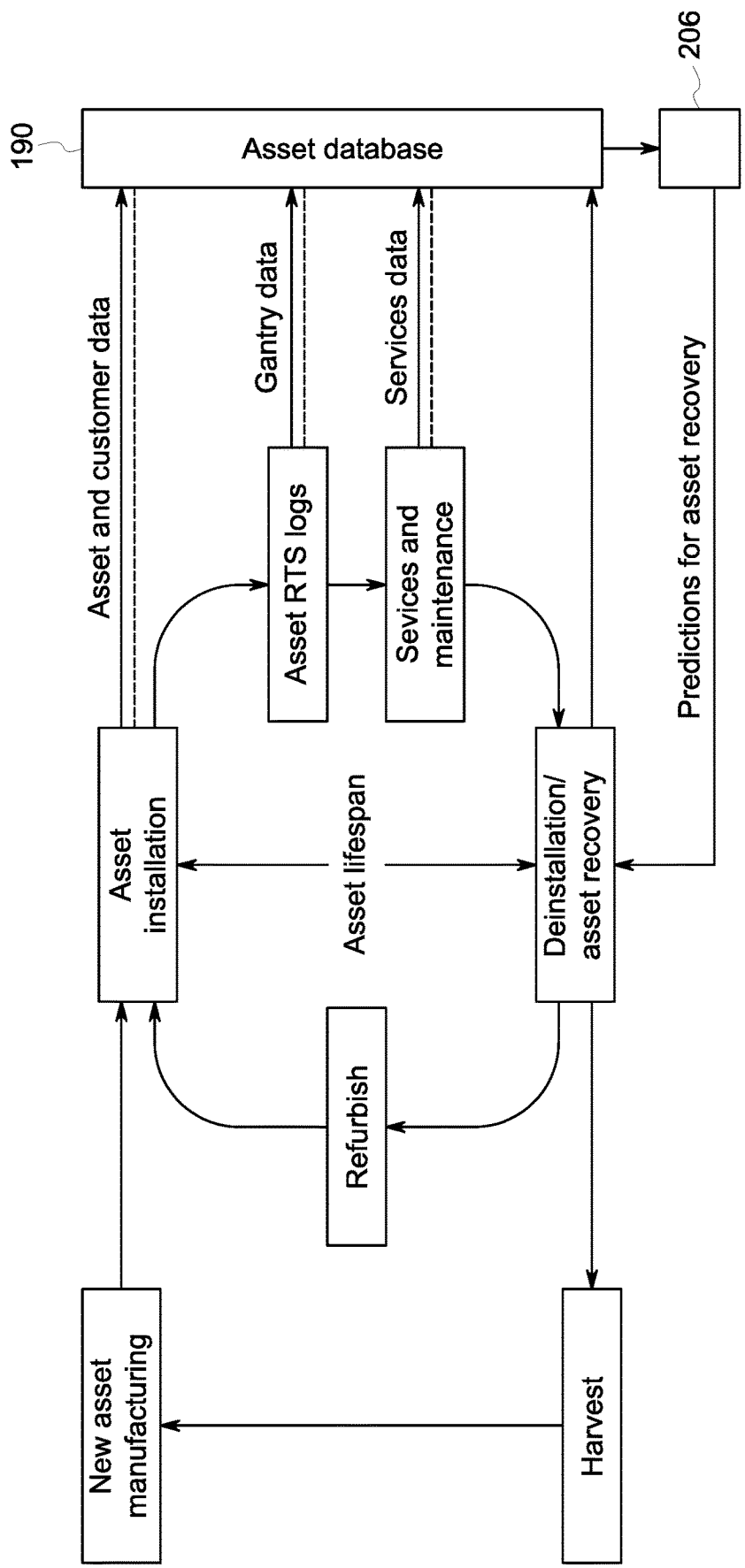
FIG. 4 is a flow chart depicting asset lifespan and machine data inputs for an asset recovery model.

Asset data is collected about each asset throughout the life cycle of that asset. FIG. 4 depicts an exemplary asset lifecycle at asset installation, where the healthcare asset is installed at the healthcare facility asset and customer data is collected. The asset data collection starts at the time of manufacturing the assets, such as the manufacture date, part numbers, etc. Throughout the lifespan of the asset, between asset installation and uninstallation and/or asset recovery, further asset data is collected, such as the asset RTS logs providing information about asset usage. Services and maintenance data is also collected, such as service logs inputted by service technicians, etc. The asset recovery module 206 processes such data and provides predictions for asset recovery date and identifies recovery targets based on large amounts of data collected and stored in the asset database 190. For those assets that are recovered, information is also collected regarding the uninstallation and asset recovery, including when the asset was uninstalled, its function at the point of uninstallation, whether it was recovered, etc. Asset data may further be collected about an asset after uninstallation, such as whether the asset was refurbished and resold or whether parts were harvested for asset maintenance and/or new asset manufacturing.

Figure 2:
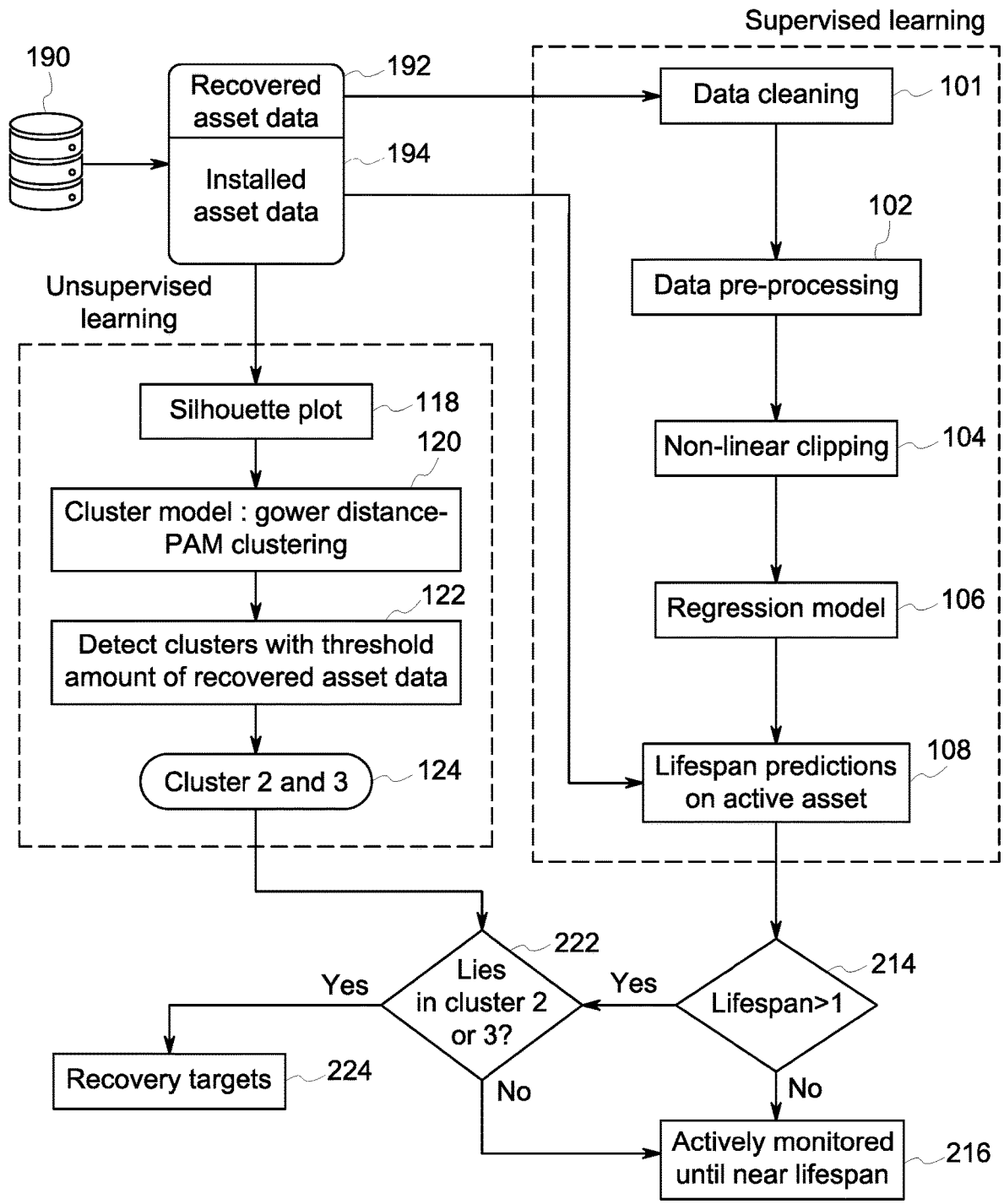
FIG. 2 depicts a flow chart demonstrating an embodiment of a system and method for monitoring installed healthcare assets.

Thus, the asset database 190 includes information about both installed assets and uninstalled assets. Of the uninstalled assets, certain assets will be recovered and others will not. Referring again to FIG. 2, the system may be configured to separate or identify recovered asset data 192 describing assets that have been recovered. The recovered asset data 192 is then used as benchmark or training data for identifying recovery target assets. As described above, both supervised and unsupervised learning are utilized in parallel to process the asset data in order to identify recovery target assets. A regression model 210 is trained on the recovered asset data 192. Prior to such training, the data is cleaned and preprocessed. Data cleaning occurs at step 101 to remove invalid data sequences, such as service records for planned maintenance where no relevant services were performed and/or to remove unrecovered asset data describing assets that were not successfully recovered. The purpose of the data cleaning step is to only include data descriptive of assets that were recovered and, to the extent possible, only include data that is likely relevant to such recovery.

Data preprocessing then occurs at step 102. In one embodiment, the data is divided into time-segments, wherein each time-segment is a percentage of lifespan of the recovered healthcare asset. FIG. 5 illustrates one such example, where, for a particular healthcare asset (system ID 2763658) the feature data for that asset are divided into a predetermined number of time-segments. In this example, the feature values are divide into 10 time-segments, each time-segment representing 10% of the lifespan of that asset. Thus, the first time-segment corresponds to and includes feature data relevant to the first 10% of the lifespan of the asset, the second time-segment includes feature values that correspond to the first 20% of the assets' lifespan, etc. Each time-segment of the machine or time-state, features are calculated up to that point of time and the corresponding label for that state is the fraction of lifespan completed. Thus, for example, segment one includes all features up to the first 10% of the assets lifespan. Segment two includes all features up to the first 20% of the assets lifespan. Similarly, segment 10 includes all features up to 100% of the assets lifespan.

Figure 6:
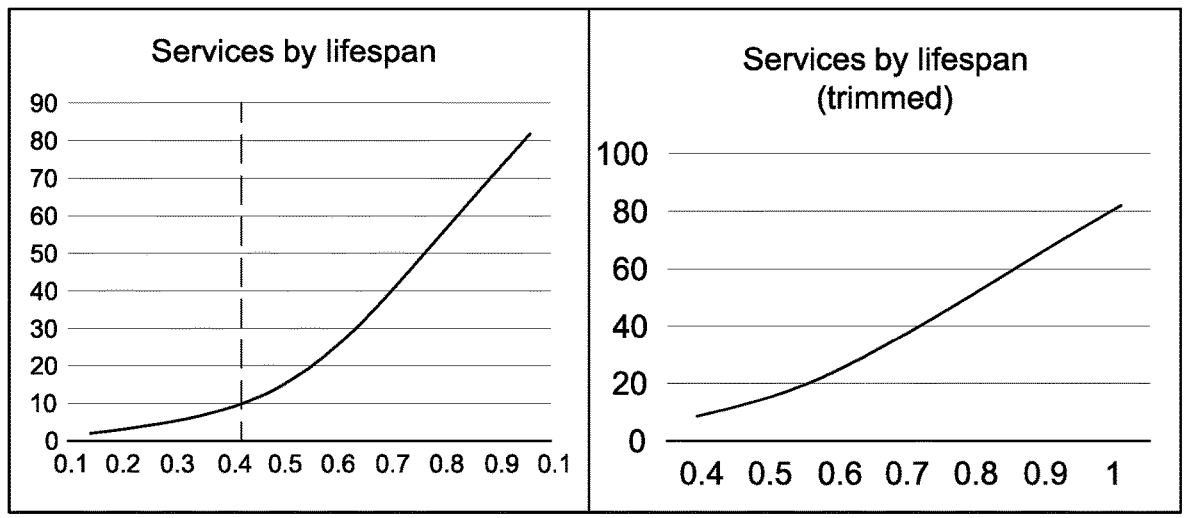
FIG. 6 is a graph illustrating a model of asset services over the asset lifespan.

In certain embodiments, the data may be filtered to increase linearity of the data, and thus non-linear clipping may be performed at step 104. For example, data relating to services performed in the initial portion of the assets lifespan may be removed. To provide just one example, feature values relating to services performed in an initial 40% of the assets lifetime may be removed. FIG. 6 graphically illustrates this concept where services performed in the initial 40% of the asset lifespan are nonlinear with the services performed in the last 60% of the asset lifespan. As the number of services initially are typically very few for all assets unless that asset is faulty, the data in the first 40% of lifespan is minimal and often represent outliers because assets typically do not fail within the first 40% of lifespan. The average service data then grows with age and is approximately linear. Thus, removing the initial percentage, such as 40%, of service data over the asset lifespan improves linearity and provides better data for training the regression model. A linear regression model is then trained at step 106 on the processed recovered asset data. For example, the regression model may be trained on the recovered asset data using the following regression loss function:

$$\text{Loss Function} = \frac{\sum_{i=1}^{n}\left[(W^T X + b) - y\right)^2}{n}$$

The resulting trained regression model 210 is a linear regression model configured to predict remaining lifespan for an asset. The lifespan of the asset is predicted at step 108 by applying the trained regression model 210 to installed asset data 194 describing currently-installed assets at healthcare facilities (e.g. 18a, 18b). For example, the model may output a number between zero and one where zero is a brand new asset and one represents an entire lifespan of the asset. Any value exceeding one represents that the asset is exceeding its expected lifespan, and thus is being overused and should be recovered immediately.

Step 214 determines whether the asset has reached or exceeded its lifespan or has remaining lifespan for the asset. For example, if the output of the regression model is at least (or in some embodiments greater than) one, than the asset is considered to have reached its lifespan and may be ripe for recovery and thus may be identified as a target asset pending further qualifications. If the output of the trained regression model 210 is less than one, or otherwise indicates that the asset has not yet reached its lifespan, then the asset is actively monitored at step 216 until it nears the end of its lifespan. Those assets that have reached a threshold lifespan value identified for step 214 are then passed to step 222.

In contrast to the supervised learning that occurs with the trained regression model 210, unsupervised learning is utilized to identify which assets have qualities indicating that they should be recovered. Thus, whereas the trained regression model 210 is utilized to predict product lifespan and thus when an asset should be recovered, the unsupervised clustering model 208 is utilized to identify which assets have qualities indicating that the asset is likely to be available for recovery. A silhouette plot is performed at step 118 to plot a silhouette coefficient fork to find an optimal number of clusters. For example, the number of clusters may be confined to a range between two and eight clusters. In other embodiments, other upper and lower constraints may be used.

A clustering model is then utilized at step 120 to cluster the recovered asset data 192 and the installed asset data 194 into the optimal number of clusters identified at step 118. For example, a PAM clustering model (K-medoids) algorithm may be utilized. In contrast to centroid assignment performed in K-Means clustering, PAM clustering utilizes actual data points (medioids) as the centers. Thus, PAM clustering so more robust to noise and outliers as compared to K-Means, and thus gives better results for the asset data regarded herein. To find the optimal number of clusters for the dataset, Gower distance was used as the distance metric. Gower distance is a measure of how similar an object is to its own cluster compared to other clusters. Gower distance may be utilized, such as instead of Euclidean distance, because Gower distance works well with datasets that contain both numerical and categorical data. The Gower distance calculates partial similarities between data points according to the following formula:

$$d(i, j) = \frac{1}{p}\sum_{i=1}^{p} d_{ij}^{(f)}$$

Figure 7:
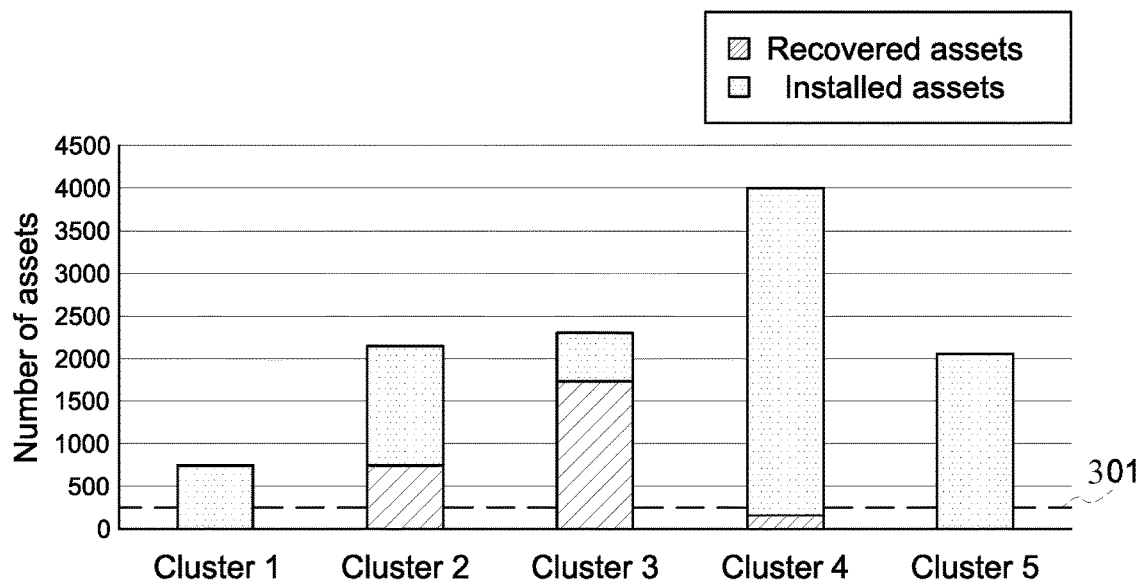
FIG. 7 is a graph representing exemplary clustering of installed asset data and recovered asset data by a clustering model.

From the optimal number of clusters formed at step 120, which in this particular example is five clusters, a subset of clusters is identified at step 122 as those clusters containing at least a threshold amount of recovered asset data. FIG. 7 depicts an exemplary set of five clusters generated by an exemplary clustering model. Of the five clusters, only three contain any recovered asset data. Of the three clusters that contain asset data, only two contain recovered asset data regarding a sufficient number of assets—i.e., above the threshold number of assets 301. Thus, in the example, cluster four does not contain at least the threshold amount of recovered asset data, whereas clusters two and three do include at least the threshold amount of recovered asset data. Thus, clusters two and three are identified at step 124 and the installed asset data included in those clusters is identified as a set of target assets that are likely recoverable (at an appropriate time determined by the trained regression model 210).

At step 222 the set of target assets is compared with the list of assets that have reached the end of their lifespan in order to generate recovery target assets, which are outputted at step 224. For example, this may be a list of assets to be recovered within a future timeframe. FIG. 8 depicts an exemplary list of recovery target assets, which identify those installed assets that have reached the end of their lifespan (as identified by the trained regression model 210, and match patterns identified in the recovered assets (identified by the trained cluster model 208)). Various information may be provided about each recovery target asset, such as region, timeframe (such as year and quarter), when the asset should be recovered, which cluster that asset belonged to, the asset age, the installed date, the installed location, the asset type, etc. This list can then be used by a party to recover healthcare assets and or to sell new healthcare assets to replace those recovered healthcare assets.

This written description uses examples to disclose the invention, including the best mode, and also to enable any person skilled in the art to make and use the invention. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

I claim:

1. A system for monitoring installed healthcare assets, the system comprising:
    an asset database containing installed asset data and recovered asset data, wherein the installed asset data comprises feature values describing installed healthcare assets and recovered asset data comprises feature values describing uninstalled healthcare assets that were recovered wherein monitoring the installed healthcare assets includes monitoring at least one of a computer tomography (CT) imager, a magnetic resonance (MR) imager, a positron emission tomography (PET) imager, or a combination thereof;
    a storage system storing a trained regression model and a clustering model;
    a processing system configured to:
        process the installed asset data using the trained regression model to predict a recovery time for each installed healthcare asset;
        process the installed asset data and the recovered asset data using the clustering model to identify a set of target assets, wherein the set of target assets is subset of the installed healthcare assets;
        identify at least one recovery target asset based on the set of target assets and the predicted recovery time for each installed healthcare asset in the set of target assets; and
        output to a user using the processing system an identifier of the at least one recovery target asset to be recovered.

2. The system of claim 1, wherein the trained regression model is a linear regression model configured to predict a lifespan of a healthcare asset based on at least one of the feature values describing the healthcare asset.

3. The system of claim 2, wherein the recovery target asset is an installed healthcare asset having an asset age greater than or equal to the predicted lifespan, wherein the lifespan of a healthcare asset is a time period between asset install date and asset uninstall date.

4. The system of claim 1, wherein the processing system is further configured to:
    process the installed asset data and the recovered asset data using the clustering model to divide the installed asset data and the recovered asset data into clusters;
    identify a subset of the clusters containing at least a threshold amount of each of the installed asset data and the recovered asset data; and
    identify the set of target assets based on the installed asset data in the subset of the clusters.

5. The system of claim 1, wherein the clustering model utilizes a partitioning around medoids (PAM) algorithm and Gower distance.

6. The system of claim 1, wherein the trained regression model is trained using recovered asset data comprising feature values describing uninstalled healthcare assets that were recovered.

7. The system of claim 6, wherein asset data describing uninstalled healthcare assets that were not recovered is excluded from training data for the trained regression model.

8. The system of claim 6, wherein the feature values in the recovered asset data used as training data for the trained regression model are divided into a predetermined number of time-segments, wherein each time-segment is a percentage of a lifespan of the recovered healthcare asset.

9. The system of claim 1, wherein the installed asset data includes feature values describing at least one of an asset age of the installed healthcare asset, a service history of the installed healthcare asset, a facility where the installed healthcare asset is located, operation history of the installed healthcare asset, and customer demographics of a customer owning the installed healthcare asset, and wherein the installed asset data includes feature values describing assets from at least two different vendors.

10. The system of claim 9, wherein the feature values describing the operation history include a number of scans and/or total scan time performed by the installed healthcare asset.

11. A computer-implemented method of monitoring installed healthcare assets, the method comprising:
    monitoring installed healthcare assets including at least one of a computer tomography (CT) imager, a magnetic resonance (MR) imager, a positron emission tomography (PET) imager, or a combination thereof to generate healthcare asset data;
    storing the healthcare asset data that includes installed asset data comprising feature values describing the installed healthcare assets and recovered asset data comprising feature values describing uninstalled healthcare assets that were recovered;
    using a trained regression model, executed in a processing system predicting a recovery time for each installed healthcare asset based on the installed asset data;
    using a clustering model, executed in the processing system identifying a set of target assets based on the installed asset data and the recovered healthcare data, wherein the set of target assets is subset of the installed healthcare assets;
    identifying at least one recovery target asset based on the set of target assets and the predicted recovery time for each installed healthcare asset in the set of target assets; and outputting to a user using the processing system an identifier of the at least one recovery target asset to be recovered.

12. The method of claim 11, wherein the trained regression model is a linear regression model configured to predict a lifespan of a healthcare asset based on at least one of the feature values describing the healthcare asset, wherein the recovery target asset is an installed healthcare asset having an asset age greater than or equal to the predicted lifespan.

13. The method of claim 11, wherein identifying the set of target assets includes:
dividing the installed asset data and the recovered asset data into clusters using the clustering model;
identifying a subset of the clusters containing at least a threshold amount of each of the installed asset data and the recovered asset data; and
identifying the set of target assets based on the installed asset data in the subset of the clusters.

14. The method of claim 11, further comprising training a linear regression model using recovered asset data comprising feature values describing uninstalled healthcare assets that were recovered.

15. The method of claim 14, further comprising excluding asset data describing uninstalled healthcare assets that were not recovered from training data prior to training the regression model.

16. The method of claim 14, further comprising dividing the feature values in the recovered asset data used as training data into a predetermined number of time-segments, wherein each time-segment is a percentage of a lifespan of the recovered healthcare asset.

17. The method of claim 16, wherein the lifespan of each healthcare asset is a time period between asset install date and asset uninstall date of the respective uninstalled healthcare asset.

18. The method of claim 16, further comprising removing feature values relating to services performed in at least a first time segment from training data prior to training the regression model.

19. A computer-implemented method of predicting a recovery time for an installed healthcare asset, the method comprising:
storing installed healthcare asset data, wherein the installed asset data comprises feature values describing installed healthcare assets, wherein the installed healthcare asset includes at least one of a computer tomography (CT) imager, a magnetic resonance (MR) imager, a positron emission tomography (PET) imager, or a combination thereof;
storing recovered asset data, wherein recovered asset data comprises feature values describing uninstalled healthcare assets that were recovered;
training a linear regression model using the recovered asset data, wherein the trained regression model is configured to predict a lifespan of a healthcare asset based on at least one of the feature values describing the healthcare asset;
using the trained regression model executed in a processing system generating a predicted recovery time for each installed healthcare asset based on the installed asset data; and
outputting to a user using the processing system an identifier of the at least one recovery target asset to be recovered.

20. The method of claim 19, further comprising generating a training dataset for training the linear regression model by:
dividing the feature values in the recovered asset data into a predetermined number of time-segments, wherein each time-segment is a percentage of a lifespan of the recovered healthcare asset; and
removing feature values relating to services performed in at least a first time segment.

* * * * *